United States Patent
Soto Del Valle et al.

(10) Patent No.: US 11,937,824 B2
(45) Date of Patent: Mar. 26, 2024

(54) IMPLANT DETACHMENT SYSTEMS WITH A MODIFIED PULL WIRE

(71) Applicant: DePuy Synthes Products, Inc., Raynham, MA (US)

(72) Inventors: Ariel Soto Del Valle, Raynham, MA (US); Lacey Gorochow, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/566,287

(22) Filed: Dec. 30, 2021

(65) Prior Publication Data
US 2023/0210533 A1 Jul. 6, 2023

(51) Int. Cl.
*A61B 17/12* (2006.01)

(52) U.S. Cl.
CPC .... *A61B 17/12113* (2013.01); *A61B 17/1215* (2013.01); *A61B 2017/12054* (2013.01)

(58) Field of Classification Search
CPC .......... A61B 17/12113; A61B 17/1215; A61B 2017/12054
See application file for complete search history.

(56) References Cited

U.S. PATENT DOCUMENTS

| | | |
|---|---|---|
| 3,429,408 A | 2/1969 | Maker et al. |
| 5,108,407 A | 4/1992 | Geremia et al. |
| 5,122,136 A | 6/1992 | Guglielmi et al. |
| 5,234,437 A | 8/1993 | Sepetka |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |

(Continued)

FOREIGN PATENT DOCUMENTS

| | | |
|---|---|---|
| CN | 104203341 A | 12/2014 |
| CN | 106456422 A | 2/2017 |

(Continued)

OTHER PUBLICATIONS

Extended European Search Report issued in European Patent Application No. 22217163.9 dated May 25, 2023.

*Primary Examiner* — Darwin P Erezo
*Assistant Examiner* — Zehra Jaffri
(74) *Attorney, Agent, or Firm* — TROUTMAN PEPPER HAMILTON SANDERS LLP

(57) ABSTRACT

A detachment system for delivering an embolic coil implant to a treatment site is provided. A pull wire through a lumen of the detachment system that engages a loop wire can include a slack section. The slack section can be one or more bends, a spiral coil, or a stretchable material. The slack section is effective to inhibit premature detachment of the implantable medical device by inhibiting movement of the distal end of the pull wire when the detachment system is traversing a microcatheter.

15 Claims, 7 Drawing Sheets

(56) References Cited

U.S. PATENT DOCUMENTS

| | | |
|---|---|---|
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 | 1/2015 | Que et al. |
| 8,956,381 B2 | 2/2015 | Que et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269721 A1 | 10/2008 | Balgobin et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0312748 A1 | 12/2009 | Johnson et al. |
| 2010/0094395 A1 | 4/2010 | Kellett |
| 2010/0114017 A1 | 5/2010 | Lenker et al. |
| 2010/0206453 A1 | 8/2010 | Leeflang et al. |
| 2010/0324649 A1 | 12/2010 | Mattsson |
| 2011/0092997 A1 | 4/2011 | Kang |
| 2011/0118776 A1 | 5/2011 | Chen et al. |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0243883 A1 | 8/2014 | Tsukashima et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |

(56) References Cited

U.S. PATENT DOCUMENTS

| | | |
|---|---|---|
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalacaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1 | 6/2019 | Lorenzo et al. |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 * | 10/2019 | Lorenzo ........... A61B 17/12022 |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2021/0001082 A1 | 1/2021 | Lorenzo et al. |
| 2021/0045759 A1 | 2/2021 | Mehri et al. |
| 2021/0085498 A1 | 3/2021 | Nygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |

FOREIGN PATENT DOCUMENTS

| | | |
|---|---|---|
| EP | 1985244 A2 | 10/2008 |
| EP | 2498691 | 9/2012 |
| EP | 3092956 A1 | 11/2016 |
| EP | 3501427 A1 | 6/2019 |
| EP | 3799803 A1 | 4/2021 |
| EP | 3854321 A1 | 7/2021 |
| EP | 1188414 A1 | 3/2022 |
| JP | 2006-334408 A | 12/2006 |
| JP | 2012-523943 A | 10/2012 |
| JP | 2013-78584 A | 5/2013 |
| JP | 2014-399 A | 1/2014 |
| WO | WO 2008/064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |
| WO | WO-2020148768 A1 * | 7/2020 ........ A61B 17/12113 |

* cited by examiner

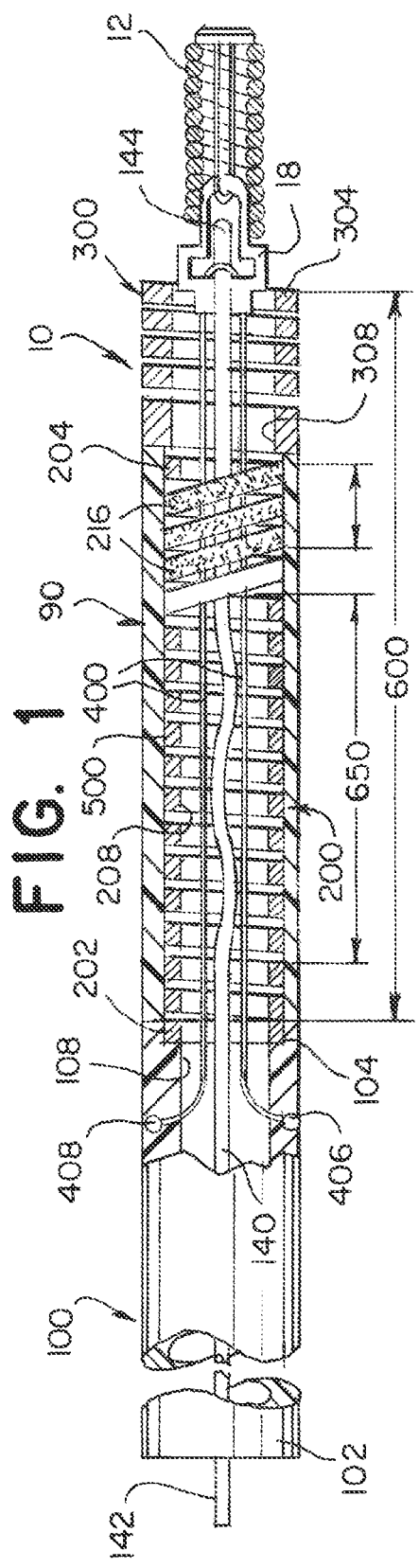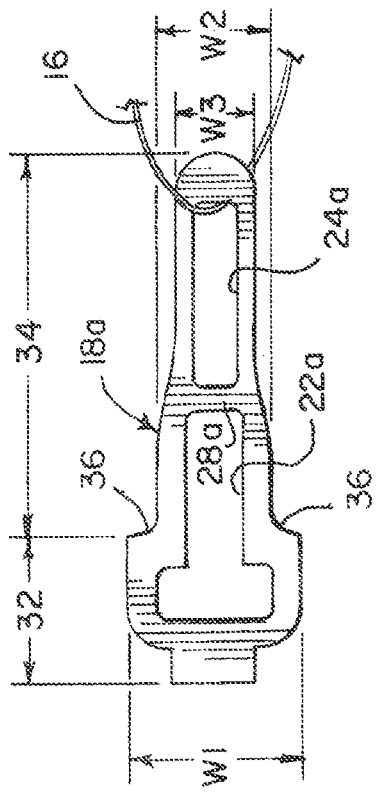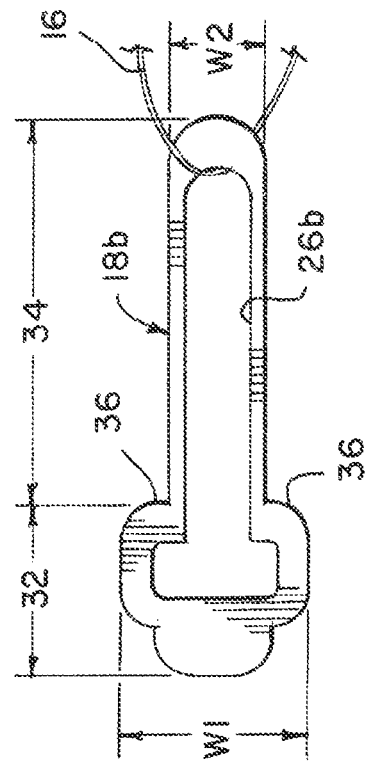

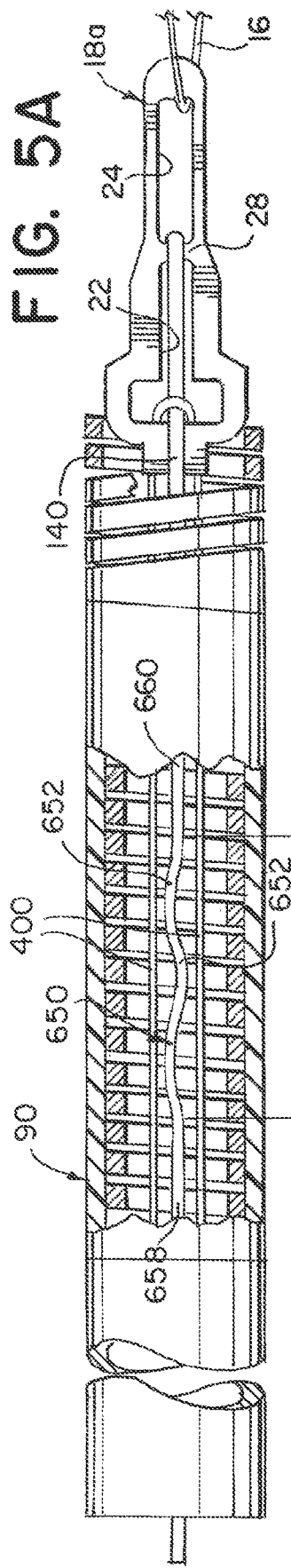
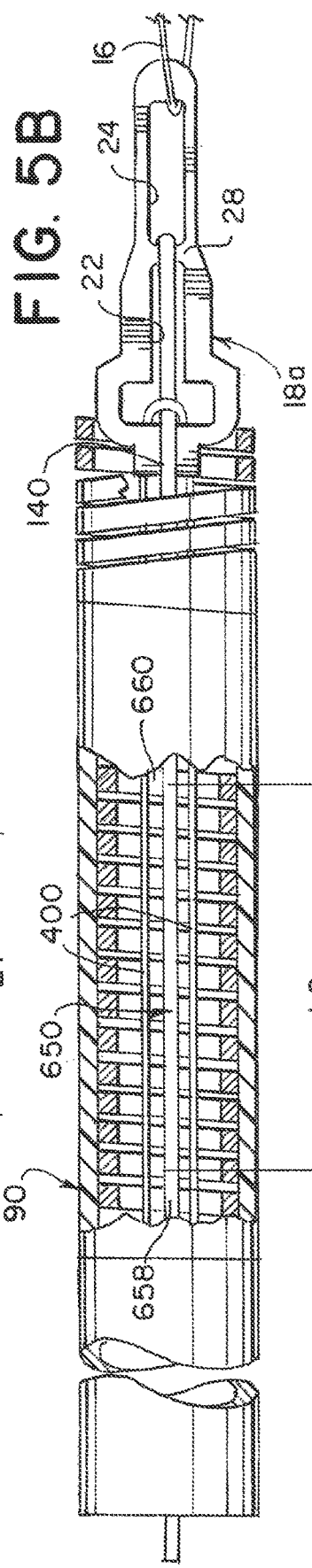
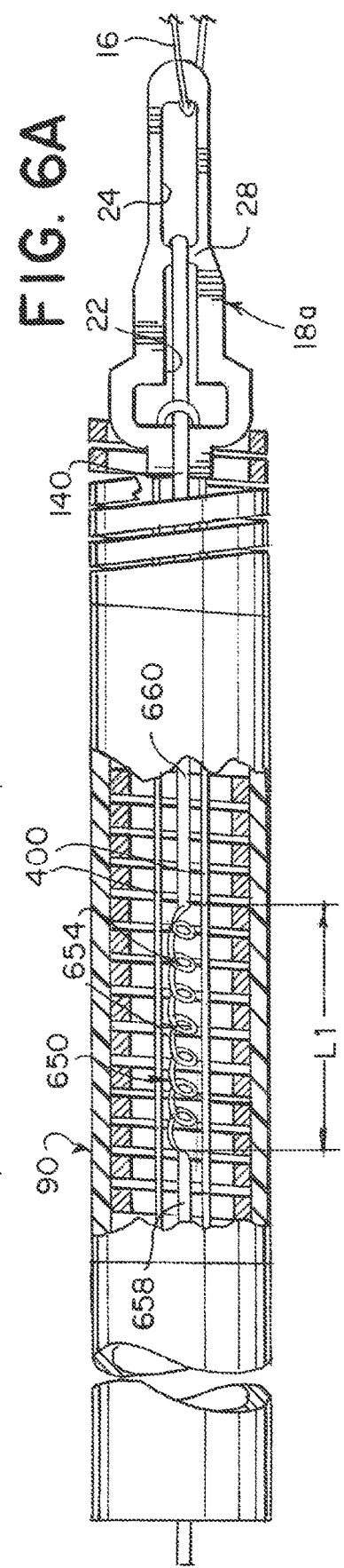

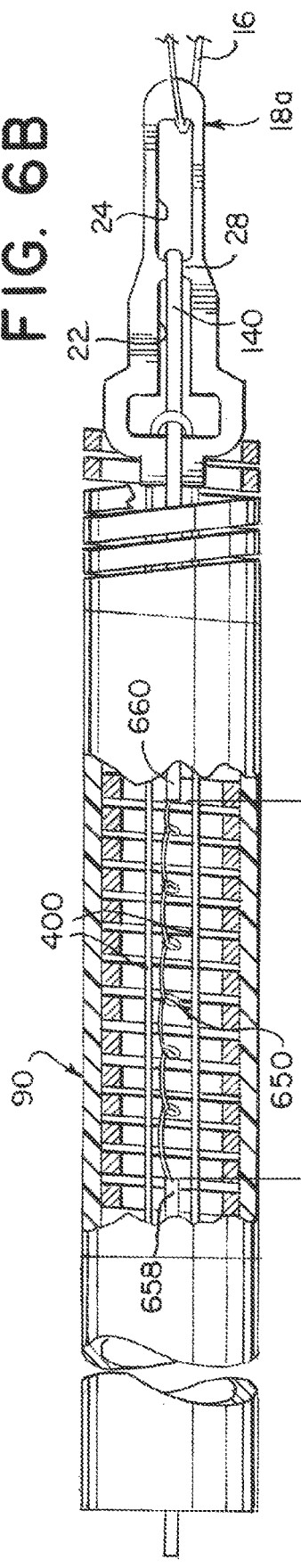
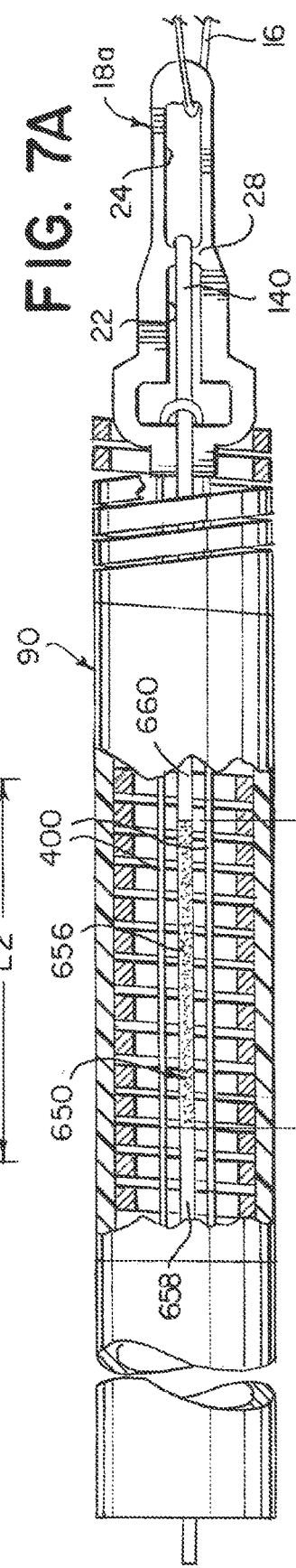
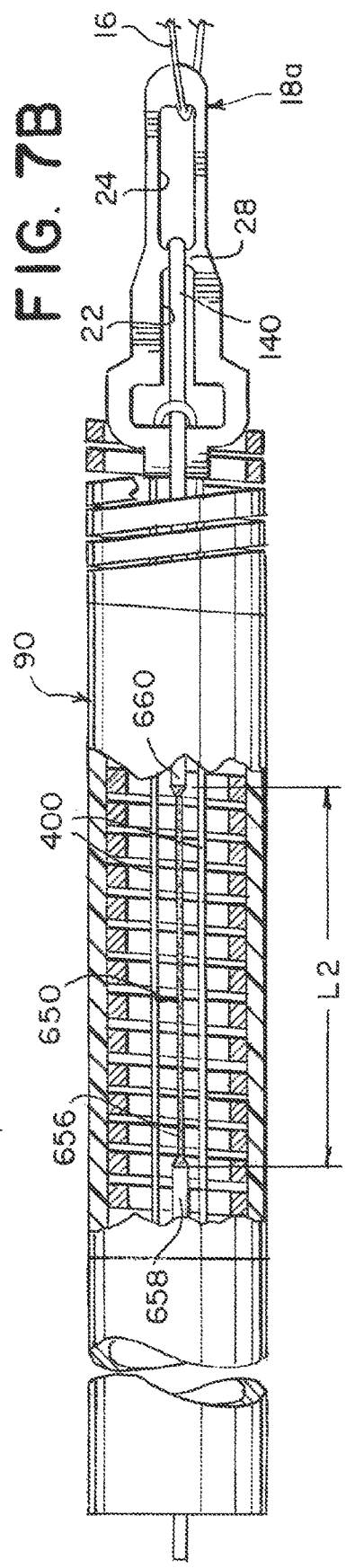

IMPLANT DETACHMENT SYSTEMS WITH A MODIFIED PULL WIRE

FIELD OF INVENTION

This invention generally relates to intravascular medical device systems that navigate through body vessels of a human subject and, more particularly, to detachment/delivery systems for delivering and deploying an implantable medical device to a target location of a body vessel and methods of using the same.

BACKGROUND

Aneurysms can be intravascularly treated by delivering a treatment device to the aneurysm to fill the sac of the aneurysm with embolic material and/or block the neck of the aneurysm to inhibit blood flow into the aneurysm. When filling the aneurysm sac, the embolic material can promote blood clotting to create a thrombotic mass within the aneurysm. When treating the aneurysm neck without substantially filling the aneurysm sac, blood flow into the neck of the aneurysm can be inhibited to induce venous stasis in the aneurysm and facilitate natural formation of a thrombotic mass within the aneurysm.

In some current treatments, multiple embolic coils are used to either fill the aneurysm sac or treat the entrance of the aneurysm neck. A common challenge among embolic coil treatments is that implanted coils and implanted portions of partially implanted coils can become entangled and difficult to reposition. In some instances, a physician may not be able to retract a partially implanted coil and may be forced to position the coil in a non-ideal location. Improperly positioning embolic coils at the aneurysm neck can potentially have the adverse effect of impeding the flow of blood in the adjoining blood vessel, particularly if the entrance and/or sac is overpacked. If a portion of the improperly placed coil becomes dislodged, it can enter the neighboring blood vessel and promote clot formation, which can ultimately lead to an obstruction that is tethered to the aneurysm and therefor extremely difficult to treat. Conversely, if the entrance and/or sac is insufficiently packed, blood flow can persist into the aneurysm.

In some current treatments, an embolic coil is attached to a tubular delivery device and delivered via a delivery catheter to an aneurysm. During delivery, the embolic coil can be engaged to the delivery member's implant detachment/deployment system (referred to herein equivalently as an "detachment system" or "deployment system"). When the embolic coil is in position, the deployment system can release the coil, the coil can be left implanted, and the delivery member can be retracted. Some treatments utilize a mechanical detachment/deployment system that can be actuated by a physician to release the implant by pulling one or more wires or other elongated members referred to generically herein as a "pull wire." Some of the challenges that have been associated with delivering and deploying embolic coils with delivery members having mechanical detachment systems include premature release of a coil due to and premature movement of the pull wire proximally, thereby releasing the coil before the system is at the treatment site. This is exacerbated because of the system moves though tortuous vasculature to the treatment site.

There is therefore a need for improved methods, devices, and systems to facilitate implantation of embolic coils and other implants facing similar challenges.

SUMMARY

It is an object of the present invention to provide systems, devices, and methods to meet the above-stated needs. In some examples presented herein, premature proximal movement or translation of a pull wire can be decreased by providing a pull wire having a slack section that allows a proximal portion of the pull wire to move independent of the distal end of the pull wire, thereby enabling a certain tolerance to proximal movement to prevent premature retraction of the pull wire through the loop wire.

A detachment system for delivering an implantable medical device to a target location of a body vessel can include a tubular body comprising a lumen extending therethrough and a compressed distal tube. The detachment system can include a loop wire comprising a first end affixed to the tubular body and comprising a loop opening positioned proximate a distal end of the compressed distal tube. The detachment system can include a pull wire extending through the lumen and through the loop opening. The pull wire can include a slack section positioned within the lumen enabling a proximal end of the pull wire to translate proximally and distally independently from a distal end of the pull wire when the detachment system is traversing a microcatheter.

The slack section can have a first length when the pull wire is in a relaxed condition and a second length when the pull wire is in a tensed condition. The distal end of the pull wire can translate proximally when the slack section exceeds the second length.

The slack section is can inhibit premature detachment of the implantable medical device by inhibiting movement of the distal end of the pull wire when the detachment system is traversing a microcatheter.

The slack section can be a plurality of bends in the pull wire positioned proximal to a location wherein the loop wire contacts the pull wire.

The slack section can be a spiral coil formed into the pull wire proximal to a location wherein the loop wire contacts the pull wire.

The slack section can be a section of stretchable material positioned along a length of the pull wire proximal to a location wherein the loop wire contacts the pull wire.

The pull wire can be defined by a proximal rigid section and a distal rigid section, and the slack section—including the stretchable material—can be positioned between the proximal rigid section and the distal rigid section, wherein the proximal rigid section and the distal rigid section as a lower degree of elasticity than the section of stretchable material.

The section of stretchable material can be a polymeric suture.

The detachment system can include a key affixed to the implantable medical device proximate a proximal end of the implantable medical device. The key can include a distal opening therethrough, wherein a stretch resistant fiber passes through the distal opening. The key can include a proximal opening therethrough. The key can include a bridge separating the distal opening and the proximal opening. The stretch resistant fiber can be engaged to the key, extended through an implant lumen of the implantable medical device, and affixed to the implantable medical device proximate a distal end of the implantable medical device. The slack section can be positioned proximal to the key.

A detachment system for delivering an implantable medical device to a target location of a body vessel can include a pull wire extending through a tubular body of the detachment system. The detachment system can include a loop wire looped over the pull wire at a distal end of the loop wire. The pull wire can include a slack section positioned proximal to a loop opening in the loop wire. The slack section can inhibit premature detachment of the implantable medical device by inhibiting movement of a distal end of the pull wire when the detachment system is traversing a microcatheter.

The slack section can have a first length when the pull wire is in a relaxed condition and a second length when the pull wire is in a tensed condition. The distal end of the pull wire can translate proximally when the slack section exceeds the second length.

The slack section can be a plurality of bends in the pull wire positioned proximal to a location wherein the loop wire contacts the pull wire.

The slack section can be a spiral coil formed into the pull wire proximal to a location wherein the loop wire contacts the pull wire.

The slack section can be a section of stretchable material positioned along a length of the pull wire proximal to a location wherein the loop wire contacts the pull wire.

The pull wire can be defined by a proximal rigid section and a distal rigid section, and the slack section, including the stretchable material, can be positioned between the proximal rigid section and the distal rigid section, wherein the proximal rigid section and the distal rigid section as a lower degree of elasticity than the section of stretchable material.

The section of stretchable material can be a polymeric suture. The detachment system can a key affixed to the implantable medical device proximate a proximal end of the implantable medical device. The key can include a distal opening therethrough, wherein a stretch resistant fiber passes through the distal opening. The key can include a proximal opening therethrough. The key can include a bridge separating the distal opening and the proximal opening. The stretch resistant fiber can be engaged to the key, extended through an implant lumen of the implantable medical device, and affixed to the implantable medical device proximate a distal end of the implantable medical device. The bridge can support a portion of the pull wire in a distal direction from the loop opening. The slack section can be positioned proximal to the key.

A method as described herein can include providing a tubular body comprising a lumen extending therethrough and a compressible distal tube. The method can include affixing a loop wire to the tubular body. The method can include compressing the compressible distal tube. The method can include positioning a loop opening in the loop wire approximate a distal end of the compressible distal tube while the loop wire is affixed to the tubular body such that the loop wire is extended through the lumen. The method can include extending a pull wire through the lumen. The method can include extending the loop opening through a key of an implantable medical device. The method can include extending a distal end of the pull wire through the loop opening. The method can include forming a slack section of the pull wire to inhibit premature detachment of the implantable medical device by inhibiting movement of the distal end of the pull wire when the tubular body is traversing a microcatheter.

The slack section can have a first length when the pull wire is in a relaxed condition and a second length when the pull wire is in a tensed condition, wherein the distal end of the pull wire translates proximally when the slack section exceeds the second length. The method can further include releasing the implantable medical device when the pull wire is retracted such that a final length of the slack section exceeds the second length.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive systems and devices, by way of example only, not by way of limitation.

FIG. 1 is an illustration of a delivery/detachment system and implant, according to aspects of the present invention.

FIGS. 2A and 2B are illustrations of detachment features (i.e., keys) each having a stretch resistant fiber therethrough, according to aspects of the present invention.

FIGS. 5A and 5B are illustrations of example slack sections including a plurality of slack bends, according to aspects of the present invention.

FIGS. 6A and 6B are illustrations of example slack sections including spiral coils, according to aspects of the present invention.

FIGS. 7A and 7B are illustrations of example slack sections including stretchable material, according to aspects of the present invention.

DETAILED DESCRIPTION

Figure 3A:
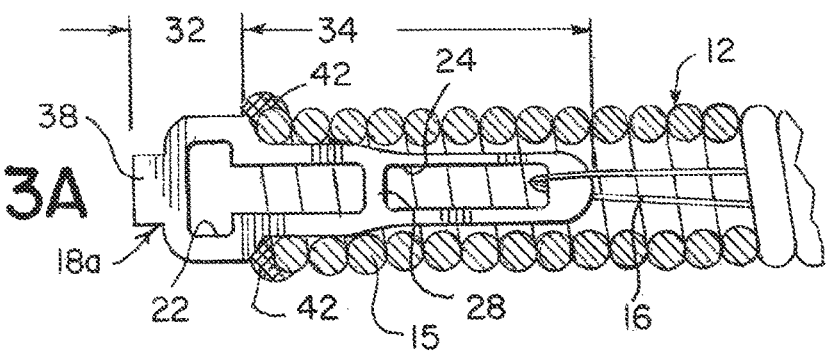
FIGS. 3A-3C are illustrations of keys affixed to an embolic coil, according to aspects of the present invention.

An object of the present invention is to decrease the occurrence of or ultimately to prevent premature detachment of an embolic coil from a detachment system prior to placing the coil at a treatment site, i.e., an aneurysm. More specifically, it is an object of the present invention to provide an amount of provide an amount of tolerance to the movement of a pull wire to ensure a distal portion of the pull wire does not inadvertently translate proximally to deploy the embolic implant. Certain current designs for embolic coil delivery systems can include a tubular body having a compressed distal tube that, once released from compression, delivers the embolic coil to a treatment site. Within that distal tube (also referred to herein as a "distal hypotube") passes both a loop wire and a pull wire. The loop wire can extend into a detachment features (also referred to herein as a "key") of the implant and loop onto the pull wire to secure the distal hypotube into its compressed state, while also containing the embolic coil that is attached to the key. One common pitfall to prior designs is that there is a chance that the pull wire can prematurely translate proximally from the loop wire, for example as a physician is delivering the device through tortuosity and reactive frictional forces cause the pull wire to retract. Premature detachment of the embolic coil from the detachment system can be a significant problem, as the physician no longer controls the timing/position of the placement of the embolic coil at the aneurysm. The present devices, systems, and methods provide a solution to early, inadvertent deployment of the embolic coil.

Referring to the figures, FIG. 1 is an illustration of a delivery/detachment system 10 and an implantable medical device 12 (which is an embolic coil in the example shown), according to aspects of the present invention. The implantable medical device 12 is also referred to herein as implant 12. The detachment system 10 can include a proximal tube 100, a coiled section 600 comprising a support coil 200, a distal tube 300, a sleeve 500 surrounding the coiled section 600, a loop wire 400 extending through the coiled section 600, and a pull wire 140 extending through the coiled section 600. A distal end 144 of the pull wire 140 can extend at least partially beyond a proximal portion of a key 18 (also referred to herein as a "detachment feature") of the implant 12. The detachment system 10 can have a tubular body 90 that is formed by the proximal tube 100, the coiled section 600 comprising the support coil 200, and the distal tube 300. When the distal tube 300 is compressed, as will be described below for when the distal hypotube 300 includes a compressible portion 306, the distal tube 300 can be referred to as a compressed distal tube.

A proximal end 102 of the proximal tube 100 can extend proximally within a delivery member (e.g., catheter 250). A distal end 104 of the proximal tube 100 can be connected to a proximal end 202 of the support coil 200. A distal end 204 of the support coil 200 can be connected to the distal tube 300 at one end, and the implant 12 can be connected to the distal tube 300 at the distal end 304 of the distal tube 300. The proximal tube 100 can include a proximal lumen 108, the coiled section 600 and support coil 200 can include a coil lumen 208, and the distal tube 300 can include a distal lumen 308. The proximal lumen 108, coil lumen 208, and distal lumen 308 provide a contiguous lumen through which the pull wire 140 and loop wire 400 pass.

The coiled section 600 can be formed primarily of a non-radiopaque material, such as steel, and can include a radiopaque section 216 made of a radiopaque material, such as platinum and/or tungsten. The radiopaque section 216 can be positioned between a proximal, non-radiopaque section of the support coil 200 and a distal, non-radiopaque section of the support coil 200. The radiopaque section 216 can be positioned a predetermined distance from a distal end 304 of the detachment system 10 so that a physician can readily visualize the placement of the distal portion of the system during a treatment procedure. The proximal section, radiopaque section 216, and distal section of the support coil 200 can be concentrically welded.

The sleeve 500 can cover at least a portion of the flexible section 106 to inhibit deformation of the flexible section and/or reduce friction with vasculature and the flexible section 106 during intravascular navigation. In some examples, the sleeve 500 can cover about 10 cm of the proximal tube 100 approximate and/or including the distal end 104 of the proximal tube 100. When the detachment system 10 is assembled, the coiled section 600 and sleeve 500 can be more flexible than the distal hypotube 300 and the proximal hypotube 100. One way to measure flexibility is to perform a three-point bend test wherein a portion of the detachment system 10 is held fixed at two end points, a force is applied perpendicularly to the detachment system 10 centrally between the points, and flexibility is quantified by the length of deflection of the detachment system 10 caused by the force. When measured this way, in some examples, the coiled section 600 and sleeve 500 can be about 1.5 times more flexible than the distal hypotube 300 and about 20 times more flexible than the proximal hypotube 100. In other words, when the three-point test is performed identically on the three sections 100, 600, 300, the coiled section 600 can deflect over a length that is about 1.5 time the deflection length of the distal hypotube 300 and about 20 times the length of deflection of the proximal hypotube 100. Flexibility can be measured in other ways as would be appreciated and understood by a person of ordinary skill in the art. When the detachment system 10 is assembled, the coiled section 600 and sleeve 500 can be more flexible than the distal hypotube and the proximal hypotube as flexibility is determined by other means as would be known to a person of ordinary skill in the art.

The loop wire 400 can be attached to the detachment system 10 at locations along the tubular body 90. The loop wire 400 can include a first end attachment 406 to connect the loop wire 400 to the wall of the lumen 108, 208, 308 and a second end attachment 408 to connect an opposite end of the loop wire 400 to the wall of the lumen 108, 208, 308. The first end attachment 406 and second end attachment 408 can be welds, adhesives, or other mechanical fasteners that connect the loop wire 400 to the tubular body 90. The first end attachment 406 and second end attachment 408 can be located along the proximal hypotube 100, as shown in FIG. 1, or any other location of the tubular body 90, including along the coiled section 600 or the proximal hypotube 300.

The pull wire 140 can include a slack section 650 positioned along length of the pull wire 140. The slack section 650 can provide an area of the pull wire 140 that can stretch and relax while the detachment system 10 is traversing through a microcatheter (e.g., catheter 250). The slack section 650 can enable the section of the pull wire 140 distal to the slack section (i.e., distal rigid section 660) to remain stationary independent from unintended movement of the pull wire proximal to the slack section (i.e., proximal rigid section 658 or the proximal end 142 of the pull wire 140). The distal rigid section 660 of the pull wire 140 is the section of the pull wire 140 that engages with the loop wire 400 to contain the implant 12. Additional details regarding the loop wire 140 and slack section 650 are provided below with reference to FIGS. 5A to 7B. The example detachment system 10 illustrated in FIG. 1 shows a slack section 650 positioned within the coil lumen 208, which is in accordance with certain examples. The slack section 650 can also be positioned at other locations along the length of the tubular body 90, for example within the proximal lumen 108 or the distal lumen 308.

As described above, one common concern with prior systems is inadvertent proximal translation of the pull wire as the system is deliver through the tortuosity. Inhibiting proximal translations of the distal rigid section 660 pull wire 140 can prevent inadvertent proximal translation of the pull wire 140. The distal tube 300 can be compressed or a portion of the distal tube 300 can be compressed such that, once the pull wire 140 is pulled laterally sufficiently to overcome the slack in the stretchable slack section 650, the distal end 144 of the pull wire 140 is removed from the loop at the end of the loop wire 40, and the compressed portion of the distal tube 300 can expand to deliver the implant 12. FIGS. 7A-7B provide a detailed view of a compressible portion 306 of the distal hypotube 300.

FIGS. 2A and 2B are illustrations of detachment features (i.e., keys 18) each having a stretch resistant fiber 16 therethrough, according to aspects of the present invention. FIG. 2A illustrates a dual opening key 18a having a proximal portion 32 that is sized to engage a mechanical detachment system 10 and/or delivery tube (e.g., the distal hypotube 300). The proximal portion 32 is illustrated as having a width W1. The dual opening key 18*a* can have a distal portion 34 that is sized to fit within a lumen 13 of the embolic coil (e.g., implant 12). The distal portion 34 can have a wider section having a width W2 that is about as wide as the inner diameter of the implant 12 and a tapered section having a width W3 that is narrower than the inner diameter of the implant 12. The dual opening key 18*a* can have a proximal tab 38 that is narrower than the proximal portion 32 and is sized to fit within a lumen of a delivery tube (e.g., distal lumen 308). The "dual opening" of the dual opening key 18*a* can refer to the two separate openings within the face of the key 18*a*, for example a proximal opening 22 and a distal opening 24. A bridge 28 can separate the proximal opening 22 and the distal opening 24, as illustrated. The bridge 28 can be used to support the distal end 144 of the pull wire 140 when the detachment system 10 is in the loaded/pre-deployed state.

FIG. 2B illustrates a single opening key 18*b* having a proximal portion 32 that is sized to engage a mechanical detachment system 10 and/or delivery tube (e.g., the distal hypotube 300). The proximal portion 32 is illustrated having a width W1. The single opening key 18*b* can have a distal portion 34 narrower than the proximal portion 32 and sized to fit within the lumen 13 of the implant 12. The single opening key 18*b* can have a proximal tab 38 that is narrower than the proximal portion 32 and sized to fit within a lumen of a delivery tube, as also shown for the dual opening key 18*a*.

When reference is made herein to a key 18, it will be understood to include a dual opening key 18*a* or a single opening key 18*b*. After the key 18 is formed, a stretch resistant fiber 16 can be threaded through a distal opening 24 of the dual opening key 18*a* or the single opening 26 of the single opening key 18*b*. The stretch resistant fiber, which can be a suture material and the like, can secure the key to the embolic coil portion of the implant. The key 18 can include engagement surfaces 36 at a distal end of the proximal portion 32 of the key 18. This engagement surfaces 36 can abut a proximal end 15 of the implant 12.

Figure 3B:
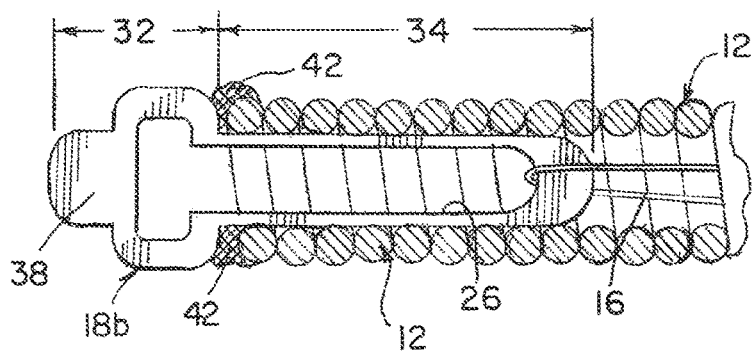
Figure 3C:
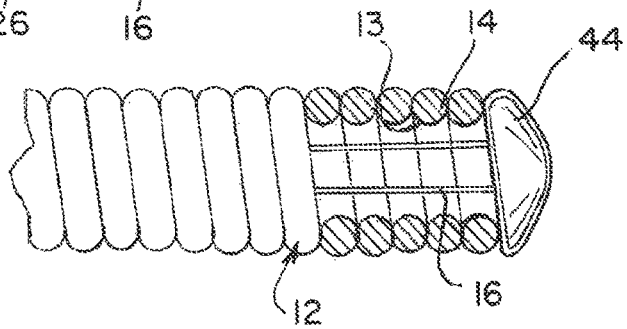

FIGS. 3A-3C are illustrations of keys 18 affixed to an embolic coil (e.g., implant 12), according to aspects of the present invention. In particular, FIGS. 3A and 3B are illustrations of the keys 18 with the distal portion 34 fully inserted into the lumen 13 of the implant 12 and wherein the key 18 is affixed to the implant 12 with welds 42 or other attachments. The welds 52 can be positioned at locations wherein the engagement surfaces 36 of the key 18 meets the proximal end 15 of the implant 12. In both FIGS. 3A and 3B, the key 18 is illustrated having a distal portion 34 that has a width over at least a portion of the length of the distal portion 34 that is about equal to the inner diameter of the lumen 13 of the implant 12.

Figure 4:
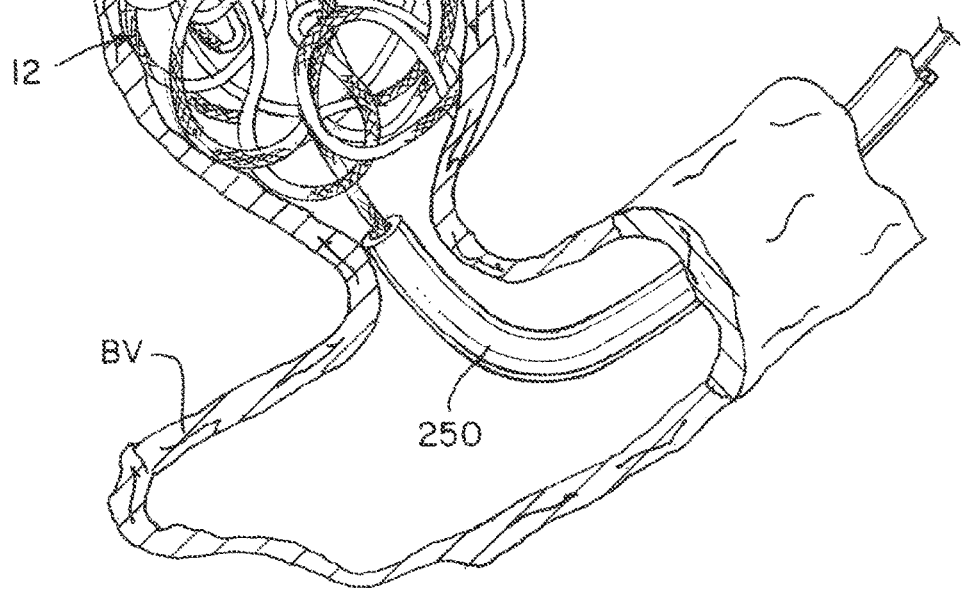
FIG. 4 is an illustration of embolic coils being positioned within an aneurysm, according to aspects of the present invention.

FIG. 4 is an illustration of embolic coils (e.g., implant 12) being positioned within an aneurysm A, according to aspects of the present invention. The detachment system 10 is passed through a blood vessels B V to the aneurysm A through a catheter 250. Once positioned, the implant(s) 12 can loop and bend within the aneurysm sac to form a thrombotic mass. The implant(s) 12 can loop back on themselves and/or loop next to other implants. As the aneurysm A becomes increasingly packed, overlapping portions of the implant 12 can press into each other.

FIGS. 5A to 7B are illustrations of example slack sections 650 in a pull wire 140, according to aspects of the present invention. The pull wire 140 can be a metallic material, such as steel, that has a degree of elasticity that allows the pull wire 140 to not only traverse the tortuosity but to also provide shape memory, and the slack section can be formed into the length of the pull wire 140, as shown in FIGS. 5A and 6A. Referring to FIG. 5A, the slack section 650 can include a series of side-to-side alternating bends 652 that can straighten when stretched and retake their original, bent state when relaxed. FIG. 5A shows the alternating bends 652 in a relaxed condition (i.e., the pull wire 140 has not been pulled proximally), and FIG. 5B shows the alternating bends 652 in a tensed condition (i.e., the pull wire 140 has been pulled proximally). The slack section 650 can have a first length L1 when the pull wire 140 is in a relaxed condition (FIG. 5A) and a second length L2 when the pull wire 140 is in a tensed condition (FIG. 5B). The distal end 144 of the pull wire 140 can translate proximally when the slack section 650 exceeds the second length L2. Stated otherwise, stretching of the slack section 650 between L1 and L2 does not translate the distal rigid section 660, and only extending the slack section 650 beyond L2 will cause the distal and 144 of the pull wire 140 to retract through the opening 405 in the pull wire 400.

Referring to FIG. 6A, the slack section 650 can include a series of spiral coils 654, like a spring, that enables the slack section 650 to stretch and shrink as the proximal rigid portion 658 moves, thereby ensuring the distal rigid section 660 does not prematurely retract from the loop wire 400. FIG. 6A shows the spiral coils 654 in a relaxed condition (i.e., the pull wire 140 has not been pulled proximally), and FIG. 6B shows the spiral coils 654 in a tensed condition (i.e., the pull wire 140 has been pulled proximally). The slack section 650 can have a first length L1 when the pull wire 140 is in a relaxed condition (FIG. 6A) and a second length L2 when the pull wire 140 is in a tensed condition (FIG. 6B). The distal end 144 of the pull wire 140 can translate proximally when the slack section 650 exceeds the second length L2, as stated above.

Referring to FIG. 7A, the slack section 650 can be a stretchable material 656 positioned along a length of the pull wire 140. The stretchable material 656 can include a polymer suture, another synthetic or natural fiber, or the like. Similar to the bends 652 and spiral coils 654 described above, the stretchable material 656 can enable the slack section 650 to stretch and shrink as the proximal rigid portion 658 moves, thereby ensuring the distal rigid section 660 does not prematurely retract from the loop wire 400. The slack section 650 can have a first length L1 when the pull wire 140 is in a relaxed condition (FIG. 7A) and a second length L2 when the pull wire 140 is in a tensed condition (FIG. 7B). The distal end 144 of the pull wire 140 can translate proximally when the slack section 650 exceeds the second length L2, as stated above.

The distal rigid section 660, proximal rigid section 658, and slack section 650 can each comprise the same material along the length of the three sections. For example, the bends 652 and/or spiral coils 654 described above can be manufactured from the same material as the distal rigid section 660 and the proximal rigid section 658. However, the sections can include different materials. For example, the distal rigid section 660 and proximal rigid section 658 can be manufactured from a less-elastic material (i.e., higher Young's modulus) such as steel, chromium alloys, and the like. The slack section can include a more elastic material, such as titanium, nickel alloys, and the like. A more elastic slack section 650 can provide more flection and stretch at portion of the pull wire 140 so as to further decrease the chance of premature proximal translation of the distal rigid section 660 that is engaged with the loop wire 400. In the case of the slack section 650 is a stretchable material 656, the stretchable material 656 can be a different material than the distal rigid section 660 and the proximal rigid section 658.

Figure 8A:
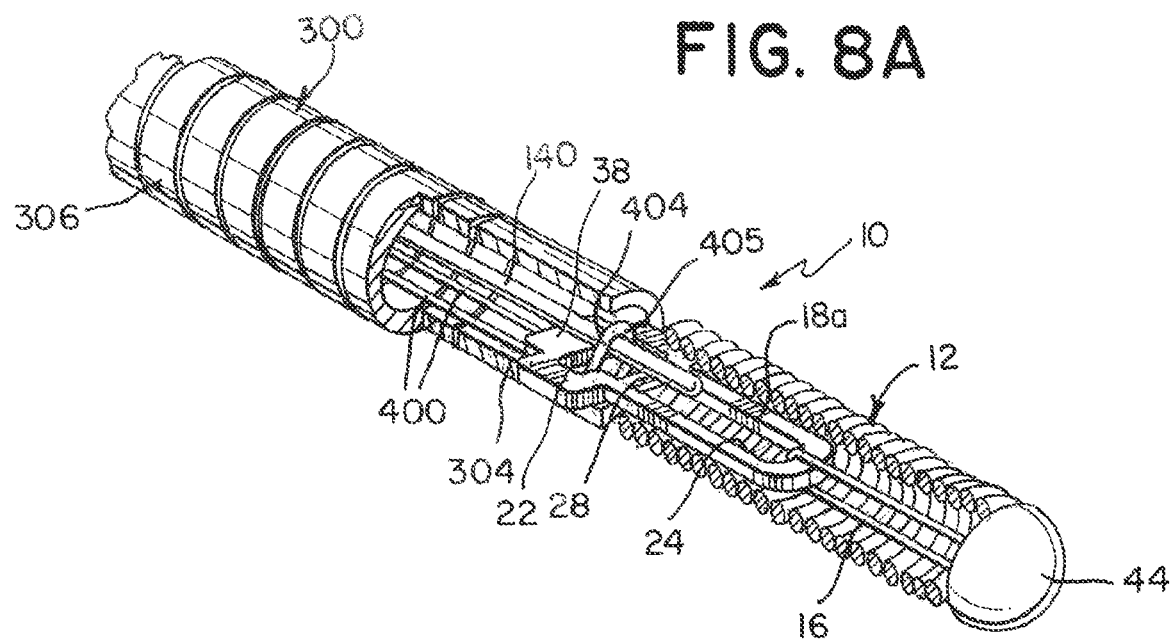
FIGS. 8A-8D illustrate a sequence of steps for releasing an embolic implant from a detachment system, according to aspects of the present invention.
Figure 8B:
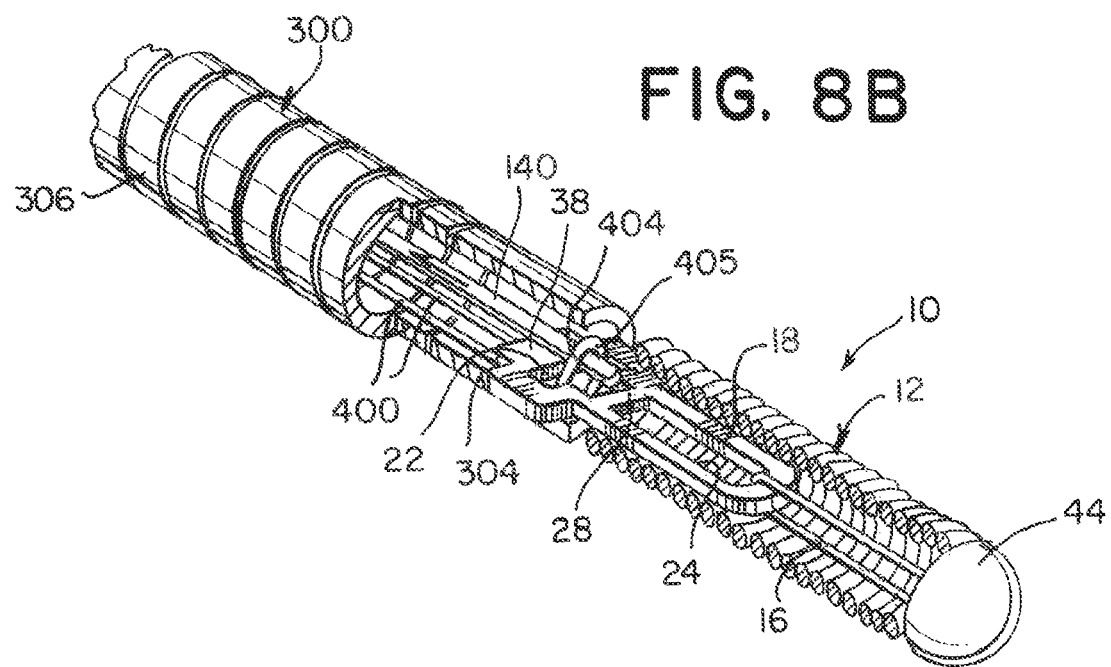
Figure 8C:
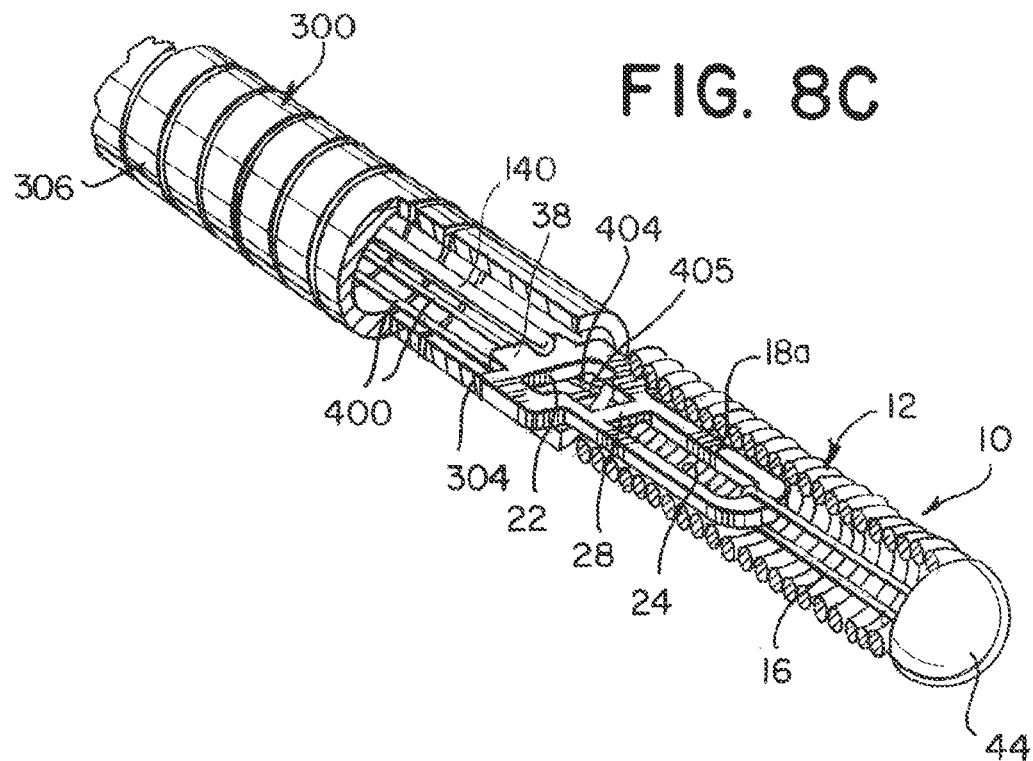
Figure 8D:
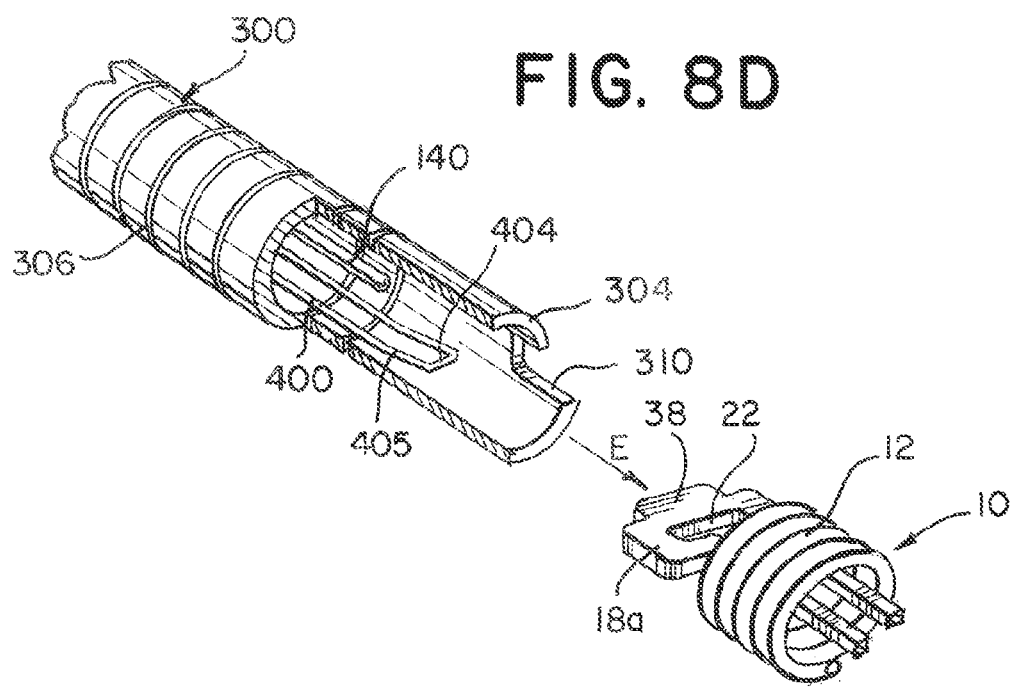

FIGS. 8A-8D illustrate a sequence of steps for releasing an embolic implant 12 from a detachment system 10, according to aspects of the present invention. FIG. 8A is an illustration of the implant 12 and delivery tube (e.g., distal hypotube 300) configured for delivery and positioning of the implant 12. FIGS. 8B through 8D illustrate releasing the example embolic implant 12 from the distal hypotube 300. A portion of the distal hypotube 300 is cut away for illustration purposes. The more proximal features of the tubular body 90 are not shown in the views.

FIG. 8A illustrates the detachment system including a pull wire 140 and a loop wire 400 locked into the key 18 of the implant 12 (the key shown in FIGS. 8A-8D is a dual opening key 18a, but the illustrations could equally apply to a single opening key 18b). The distal tube 300 can include a compressible portion 306. As described above, the slack section 650 can be proximal to the distal tube 300 in the detachment system 10, and the slack section 650 is not visible in the views shown in FIGS. 8A-8D. The loop wire 400 can have an opening 405 at a distal end 404 of the loop wire 400, and the opening 405 can be placed through an opening in the key 18 (e.g., proximal opening 22 in a dual opening key 18a, or the singular opening 26 in a single opening key 18b). When the pull wire 140 is placed through the opening 405, the implant 12 is now secure.

In the case of a dual opening key 18a, the key can include a bridge 28 positioned distally from the loop wire opening 405 and positioned to support a distal portion of the pull wire 140 that is distal of where the loop wire opening 405 wraps around by the pull wire 140. Configured thusly, the bridge 28 can support the distal portion of the pull wire 140 such that when the loop wire 400 tensions against the pull wire 140 at the loop opening 405, the bridge 28 can inhibit the distal portion of the pull wire 140 from deforming. The proximal tab 38 of the key 18 can be positioned to support a portion of the pull wire 140 that is proximal of where the loop wire opening 405 is supported by the pull wire 140. The combination of the bridge 28 and the proximal tab 38 can inhibit the pull wire 140 (i.e., the distal rigid section 660) from deforming due to forces applied by the loop wire 400. The distal hypotube 300 can be detachably attached to the implant 12 as illustrated in FIG. 8A during delivery of the implant 12 through the vasculature and while the implant 12 is being positioned at a treatment site. The bridge 28 can reduce the likelihood that the implant 12 is prematurely released due to bending of the pull wire 140 due to forces from the loop wire 400.

FIG. 8B illustrates the pull wire 140 being drawn proximally to begin the release sequence for the implant 12. As stated above, since the view shows the distal end 144 of the pull wire translating proximally, it means that sufficient tension was placed on the proximal rigid section 658 that the slack section 650 extended beyond L2 (shown in FIGS. 6A and 6B). FIG. 8C illustrates the instant the pull wire 140 exits the opening 405 and is pulled free of the loop wire 400. The distal end 404 of the loop wire 400 falls away and exits the key 18. As can be seen, there is now nothing holding the implant 12 to the distal hypotube 300. FIG. 8D illustrates the end of the release sequence. Here, the compressible portion 306 has expanded/returned to its original shape and "sprung" forward. An elastic force E is imparted by the distal end 304 of the distal hypotube 300 to the implant 12 to "push" it away to ensure a clean separation and delivery of the implant 12. The compressible portion 306 can be a spiral cut portion of the distal hypotube 300, for example a laser cut spiraled segment that can be compressed when the detachment system 10 is loaded.

Figure 9:
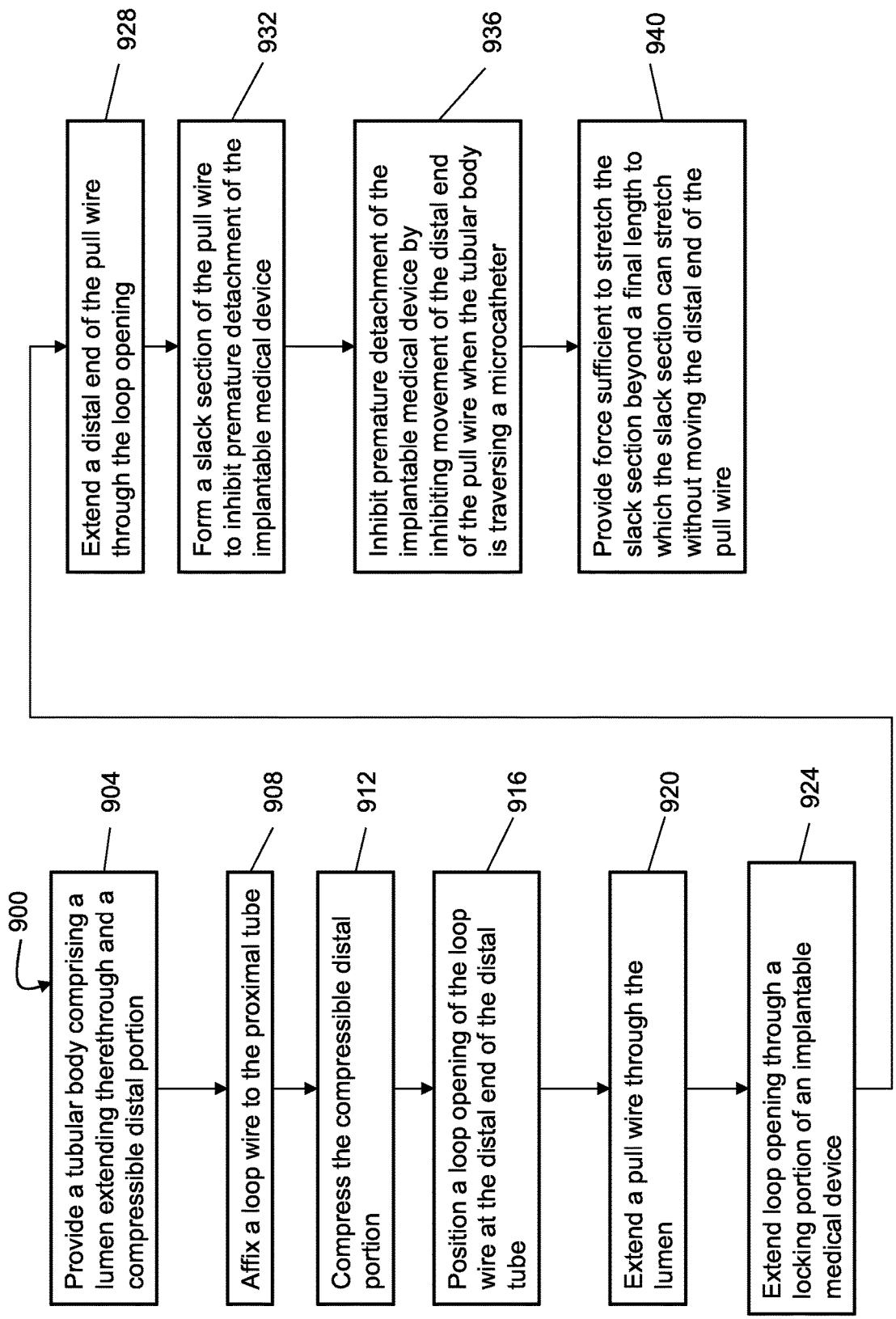
FIG. 9 is a flow diagram illustrating steps for designing, constructing, or configuring a detachment system and implant, according to aspects of the present invention.

FIG. 9 is a flow diagram illustrating a method 900 for designing, constructing, or configuring a detachment system and implant, according to aspects of the present invention. Steps 904 through 932 describe steps to create/construct one or more of detachment systems 10 described herein. In step 904, the construction of the detachment system 10 can begin with providing a tubular body 90 comprising a lumen (e.g., lumen 108, 208, 308) extending therethrough and a compressible distal tube (e.g., distal hypotube 300). In step 908, a loop wire 400 can be affixed to the tubular body 90. For example, proximal ends of the loop wire can be attached to the tubular body at a first end attachment 406 and a second end attachment 408.

In step 912, the compressible distal tube 300 can be compressed into its loaded configuration. At step 916, a loop wire opening 405 in the loop wire 400 can be positioned proximate a distal end 304 of the compressible distal tube such that the loop wire 400 is extended through the lumen (e.g., lumen 108, 208, 308). In step 920, the pull wire 140 can be extended through the lumen (e.g., lumen 108, 208, 308).

In step 924, the loop opening 405 can be extended through a key 18 of an implantable medical device 12. In step 928, a distal end 144 of the pull wire 140 can be extended through the loop opening 405 of the loop wire 140. At step 932, a slack section 650 can be formed into the pull wire 140. The slack section 650 can be any of the slack sections described herein or any similar slack section that enables the proximal end 142 of the pull wire 140 to translate proximally and distally independently from the distal end 144 of the pull wire 140 when the detachment system is traversing a microcatheter.

The steps for creating/constructing the detachment system 10 can end after step 932. In some examples, steps 936 and 940 provide additional steps to inhibit inadvertent proximal translation of the pull wire 140 and such that the implant can be deployed. For example, in step 936, proximal translation of the pull wire 140 through the loop wire 400 while the implantable medical device 12 is delivered through vasculature to a treatment site can be subdued via inhibiting movement of the distal end 144 of the pull wire 140. In step 940, sufficient force can be provided to stretch the slack section 650 beyond a final length to which the slack section 650 can stretch without moving the distal end 144 of the pull wire 140 (e.g., L2 described above).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the implant and methods for making and using the same, including alternative materials, alternative geometries of component parts, alternative positioning of component parts in relation to each other, etc. These modifications would be apparent to those having ordinary skill in the art to which this invention relates and are intended to be within the scope of the claims which follow.

What is claimed is:

1. A detachment system for delivering an implantable medical device to a target location of a body vessel, the system comprising:
   a tubular body comprising a lumen extending therethrough and a compressed distal tube;
   a loop wire comprising a first end affixed to the tubular body and comprising a loop opening positioned proximate a distal end of the compressed distal tube; and
   a pull wire extending through the lumen and through the loop opening, wherein the pull wire comprises a slack section positioned within the lumen enabling a proximal end of the pull wire to translate proximally and distally independently from a distal end of the pull wire when the detachment system is traversing a microcatheter;
   wherein the slack section is a section of stretchable material positioned along a length of the pull wire proximal to a location wherein the loop wire contacts the pull wire;
   wherein the pull wire is defined by a proximal rigid section and a distal rigid section and the section of stretchable material is positioned between the proximal rigid section and the distal rigid section, wherein the proximal rigid section and the distal rigid section has a lower degree of elasticity than the section of stretchable material.

2. The detachment system of claim 1, wherein the slack section has a first length when the pull wire is in a relaxed condition and a second length when the pull wire is in a tensed condition, wherein the distal end of the pull wire translates proximally when the slack section exceeds the second length.

3. The detachment system of claim 1, wherein the slack section is effective to inhibit premature detachment of the implantable medical device by inhibiting movement of the distal end of the pull wire when the detachment system is traversing the microcatheter.

4. The detachment system of claim 1, wherein the slack section is a plurality of bends in the pull wire positioned proximal to a location wherein the loop wire contacts the pull wire.

5. The detachment system of claim 1, wherein the slack section is a spiral coil formed into the pull wire proximal to a location wherein the loop wire contacts the pull wire.

6. The detachment system of claim 1, wherein the section of stretchable material is a polymeric suture.

7. The detachment system of claim 1, further comprising:
   a key affixed to the implantable medical device proximate a proximal end of the implantable medical device and comprising:
      a distal opening therethrough, wherein a stretch resistant fiber passes through the distal opening;
      a proximal opening therethrough; and
      a bridge separating the distal opening and the proximal opening; and
   the stretch resistant fiber engaged to the key, extended through an implant lumen of the implantable medical device, and affixed to the implantable medical device proximate a distal end of the implantable medical device,
   wherein the slack section is positioned proximal to the key.

8. A detachment system for delivering an implantable medical device to a target location of a body vessel, the system comprising:
   a pull wire extending through a tubular body of the detachment system; and
   a loop wire looped over the pull wire at a distal end of the loop wire, wherein the pull wire comprises a slack section positioned proximal to a loop opening in the loop wire, the slack section being effective to inhibit premature detachment of the implantable medical device by inhibiting movement of a distal end of the pull wire when the detachment system is traversing a microcatheter;
   wherein the slack section is a section of stretchable material positioned along a length of the pull wire proximal to a location wherein the loop wire contacts the pull wire;
   wherein the pull wire is defined by a proximal rigid section and a distal rigid section and the section of stretchable material is positioned between the proximal rigid section and the distal rigid section, wherein the proximal rigid section and the distal rigid section comprise a lower degree of elasticity than the section of stretchable material.

9. The detachment system of claim 8, wherein the slack section has a first length when the pull wire is in a relaxed condition and a second length when the pull wire is in a tensed condition, wherein the distal end of the pull wire translates proximally when the slack section exceeds the second length.

10. The detachment system of claim 8, wherein the slack section is a plurality of bends in the pull wire positioned proximal to a location wherein the loop wire contacts the pull wire.

11. The detachment system of claim 8, wherein the slack section is a spiral coil formed into the pull wire proximal to a location wherein the loop wire contacts the pull wire.

12. The detachment system of claim 8, wherein the section of stretchable material is a polymeric suture.

13. The detachment system of claim 8, further comprising:
   a key affixed to the implantable medical device proximate a proximal end of the implantable medical device and comprising:
      a distal opening therethrough, wherein a stretch resistant fiber passes through the distal opening;
      a proximal opening therethrough; and
      a bridge separating the distal opening and the proximal opening; and
   the stretch resistant fiber engaged to the key, extended through an implant lumen of the implantable medical device, and affixed to the implantable medical device proximate a distal end of the implantable medical device,
   wherein the bridge supports a portion of the pull wire in a distal direction from the loop opening, and
   wherein the slack section is positioned proximal to the key.

14. A method comprising:
   providing a tubular body comprising a lumen extending therethrough and a compressible distal tube;
   affixing a loop wire to the tubular body;
   compressing the compressible distal tube;
   positioning a loop opening in the loop wire approximate a distal end of the compressible distal tube while the loop wire is affixed to the tubular body such that the loop wire is extended through the lumen;

extending a pull wire through the lumen;

extending the loop opening through a key of an implantable medical device;

extending a distal end of the pull wire through the loop opening; and forming a slack section of the pull wire to inhibit premature detachment of the implantable medical device by inhibiting movement of the distal end of the pull wire when the tubular body is traversing a microcatheter;

wherein the slack section is a section of stretchable material positioned along a length of the pull wire proximal to a location wherein the loop wire contacts the pull wire;

wherein the pull wire is defined by a proximal rigid section and a distal rigid section and the section of stretchable material is positioned between the proximal rigid section and the distal rigid section, wherein the proximal rigid section and the distal rigid section has a lower degree of elasticity than the section of stretchable material.

15. The method of claim 14, wherein the slack section has a first length when the pull wire is in a relaxed condition and a second length when the pull wire is in a tensed condition, wherein the distal end of the pull wire translates proximally when the slack section exceeds the second length, the method further comprising:

releasing the implantable medical device when the pull wire is retracted such that a final length of the slack section exceeds the second length.

* * * * *